(12) United States Patent
Leali

(10) Patent No.: US 6,827,720 B2
(45) Date of Patent: Dec. 7, 2004

(54) SYSTEM AND METHOD FOR TREATING OSTEONECROSIS

(76) Inventor: Alejandro Leali, 1020 Warburton Ave., Yonkers, NY (US) 10701

( * ) Notice: Subject to any disclaimer, the term of this patent is extended or adjusted under 35 U.S.C. 154(b) by 0 days.

(21) Appl. No.: 10/349,126

(22) Filed: Jan. 23, 2003

(65) Prior Publication Data

US 2003/0135215 A1 Jul. 17, 2003

Related U.S. Application Data

(63) Continuation-in-part of application No. 10/050,337, filed on Jan. 15, 2002, now abandoned.

(51) Int. Cl.$^7$ ............................................... A61B 17/58
(52) U.S. Cl. ......................... 606/96; 606/101; 606/87; 606/89
(58) Field of Search ........................... 606/96, 101, 87, 606/89, 65, 66, 67, 68, 69

(56) References Cited

U.S. PATENT DOCUMENTS 6,322,565 B1 * 11/2001 Garner et al. ................. 606/96
6,607,561 B2 * 8/2003 Brannon .................... 623/23.11
2001/0039457 A1 * 11/2001 Boyer et al. ............. 623/23.52
2003/0167072 A1 * 9/2003 Oberlander ................. 606/232

* cited by examiner

Primary Examiner—Kevin Shaver
Assistant Examiner—Candice C. Melson
(74) Attorney, Agent, or Firm—LaMorte & Associates

(57) ABSTRACT

A system and method for treating a necrotic section of bone. At least one channel is drilled into a bone from a common point. Each channel has a distal end that terminates proximate the necrotic section of bone. A volume of bone growth inducing compound is introduced into each channel. The volume of bone growth inducing compound is biased toward the distal end of each channel with a screw. The screw provides immediate structural support while the bone growth inducing compound permeates the necrotic section of bone. Once the bone growth inducing compound has permeated the necrotic section of bone, it promotes rapid bone growth and thus healing of the necrotic section of bone.

13 Claims, 6 Drawing Sheets

SYSTEM AND METHOD FOR TREATING OSTEONECROSIS

RELATED APPLICATIONS

This application is a continuation-in-part of application Ser. No. 10/050,337, entitled Device For Treating And Preventing Avascular Or Osteonecrosis, filed Jan. 15, 2002 now abandoned.

BACKGROUND OF THE INVENTION

1. Field of the Invention

The present invention relates to systems and method for treating osteonecrosis that effects load bearing musculoskeletal structures.

2. Prior Art Statement

Osteonecrosis, in the form of avascular necrosis, aseptic necrosis or subchondral avascular necrosis can be caused by either disease or trauma. The most common bones effected by such a condition include the femoral head, the knee, the humeral head and the small bones of the wrist and foot. Avascular necrosis occurs when vascular fibrous tissue is deposited in an area of damaged bone. During this period, damaged, unviable bone is absorbed into the body, while new immature woven bone is deposited. As old bone is absorbed and replaced with new immature bone, the structural integrity of the bone decreases. When stressed under a load, the immature bone can mechanically fail.

When the femoral head is involved, bone failure typically happens when a section of the femoral head collapses. As a section of the femoral head collapses, the articular cartilage above the area of collapse is unsupported or under supported. The antero-lateral margin of the acetabulum (hip socket) creates an indentation in the unsupported articular cartilage, which compacts the weakened underlying subchondral bone. After structural failure of the subchondral bone, many patients require total hip replacement surgery in order to eliminate pain from the hip and to regain full mobility of the hip.

The prevalence of avascular necrosis is unknown. However, it has been estimated that between ten thousand and twenty thousand new cases develop every year in the United States.

To treat avascular necrosis in the hip, it has been attempted, in the prior art, to reinforce the weakened femoral head with bone grafts before a total hip replacement becomes necessary. The bone used in a bone graft is typically harvested from the pelvis, fibula or tibia. The harvested bone is then introduced into the femoral head through a hole that is drilled into the femoral head. Although the use of bone grafts is effective, it is not without disadvantages. The use of bone grafts causes damage in the area that the bone is harvested. The large hole drilled into the femoral head, causes weakness in the femoral neck. Long post-operative periods of rehabilitation are required in order for a patient to heal. Lastly, treatment of avascular necrosis with bone grafts requires a very complex and time consuming operating procedure.

A need therefore exists for a system and method of treating avascular necrosis in a manner that does not require bone grafts, is less detrimental to the remaining healthy sections of the effected bone and requires a simpler operating procedure. This need is met by the present invention as described and claimed below.

SUMMARY OF THE INVENTION

The present invention is a system and method for treating a necrotic section of bone. Utilizing the present invention, at least one channel is drilled into a bone from a common point. Each channel has a distal end that terminates in the subchondral bone proximate the necrotic section of bone. A volume of bone growth inducing compound is introduced into each channel. The volume of bone growth inducing compound is biased toward the distal end of each channel with a screw, wherein the bone growth inducing compound permeates the necrotic section of bone. Once the bone growth inducing compound has permeated the necrotic section of bone, the bone growth inducing compound promotes rapid bone growth and thus healing of the necrotic section of bone. Furthermore, the advancement of the screw into the channel provides instant structural support to the necrotic section of bone.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention system can be used to treat avascular necrosis in many different bones, it is particularly well suited for treating avascular necrosis in the femoral head. Accordingly, the present invention system and method will be described and illustrated in an application where the system and method are being used to treat a femoral head. Such an embodiment is exemplary and is intended only to set forth the best mode contemplated for the invention. The use of such an exemplary embodiment should not be considered as a limitation in the application of the present invention system and method to other bones.

Figure 1:
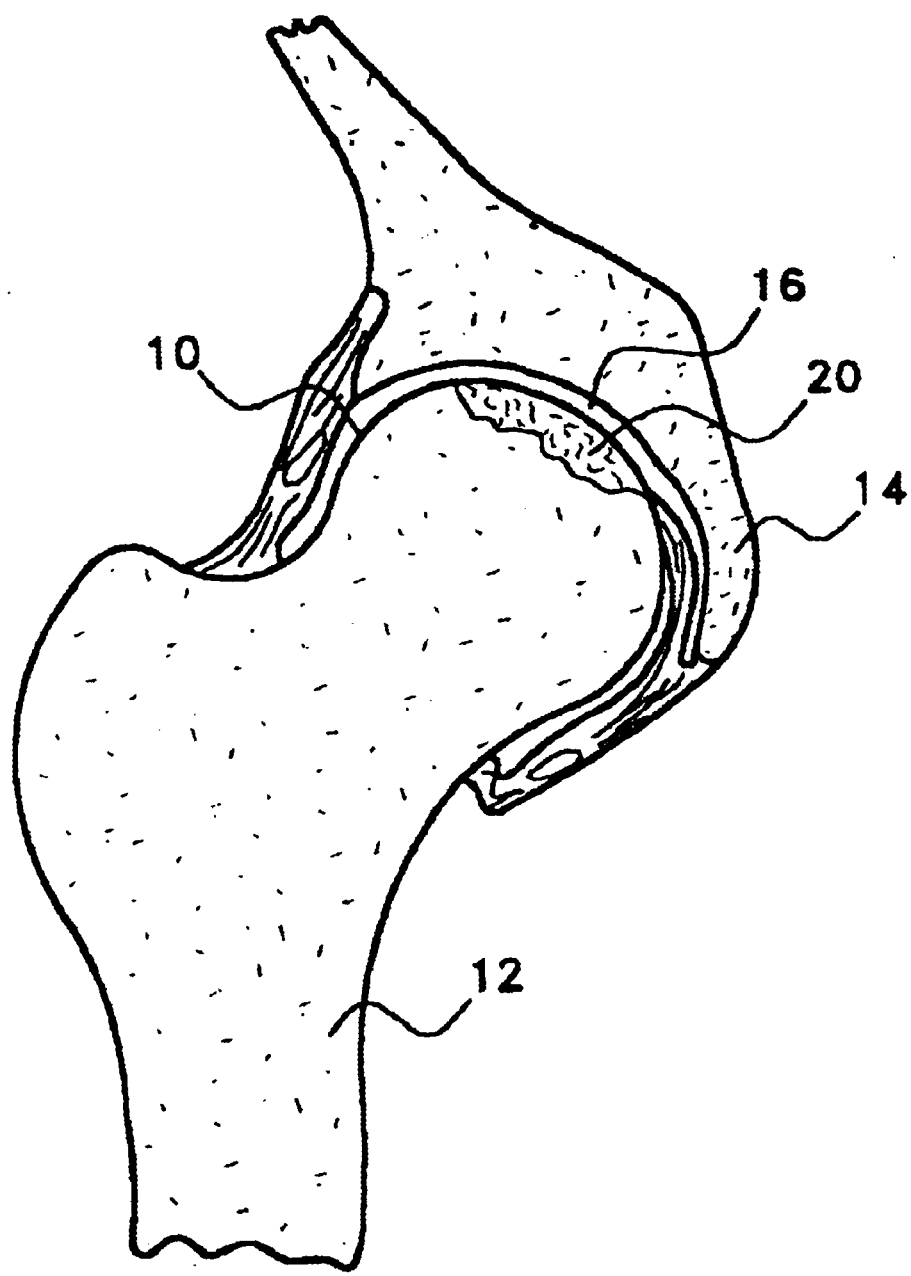
FIG. 1 shows a cross-sectional view of the hip joint of a person having a femoral head with a necrotic section.

Referring to FIG. 1, a cross section of a person's body is shown at the hip joint. From the sectional view shown, the femoral head 10 of the femur 12 is shown engaged within the acetabular fossa 14 of the pelvis, thereby creating the ball and socket structure that is the hip joint. The articular cartilage 16 is interposed between the femoral head 10 and the acetabular fossa 14.

In the shown embodiment, a section 20 of the femoral head 10 is damaged or diseased. The necrotic section 20 of the femoral head 10 is shown in its pre-collapsed stage, wherein the necrotic section 20 accounts for twenty five percent of the area of the femoral head 10.

Figure 2:
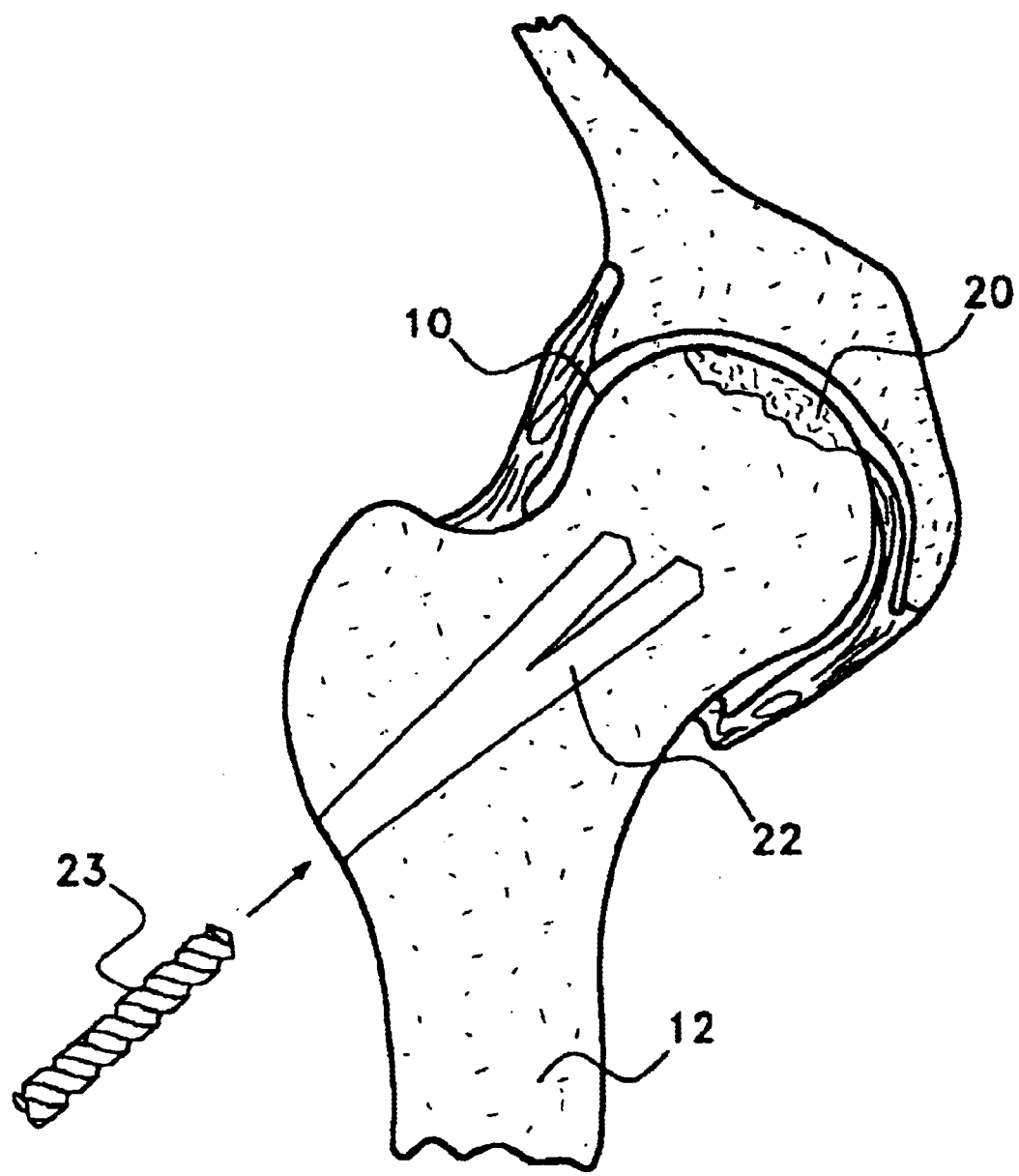
FIG. 2 is the cross-section view of FIG. 1 after having undergone the first step of the present invention treatment method.

Referring to FIG. 2, it can be seen that the first step in implementing the present invention system and method is to drill at least one channel 22 into the femur 12, using a drill bit 23. Each channel 22 is drilled by drilling into the lateral cortex of the proximal femur, through the femoral neck and into the femoral head 10. Although only a single channel can be drilled, multiple channels can also be drilled, as is illustrated. If multiple channels 22 are to be drilled, it is preferred that each of the channels 22 begin at the same entry point 24 into the femur 12. The different channels 22 diverge slightly so that each of the channels 22 extends into the femoral head 10 toward a different part of the necrotic section of bone.

The channels 22 are preferably drilled as narrowly as possible to maintain the structural integrity of the femur neck through which the channels 22 pass. Each channel 22 therefore should have a diameter of less than one centimeter and preferably less than eight millimeters.

Figure 3:
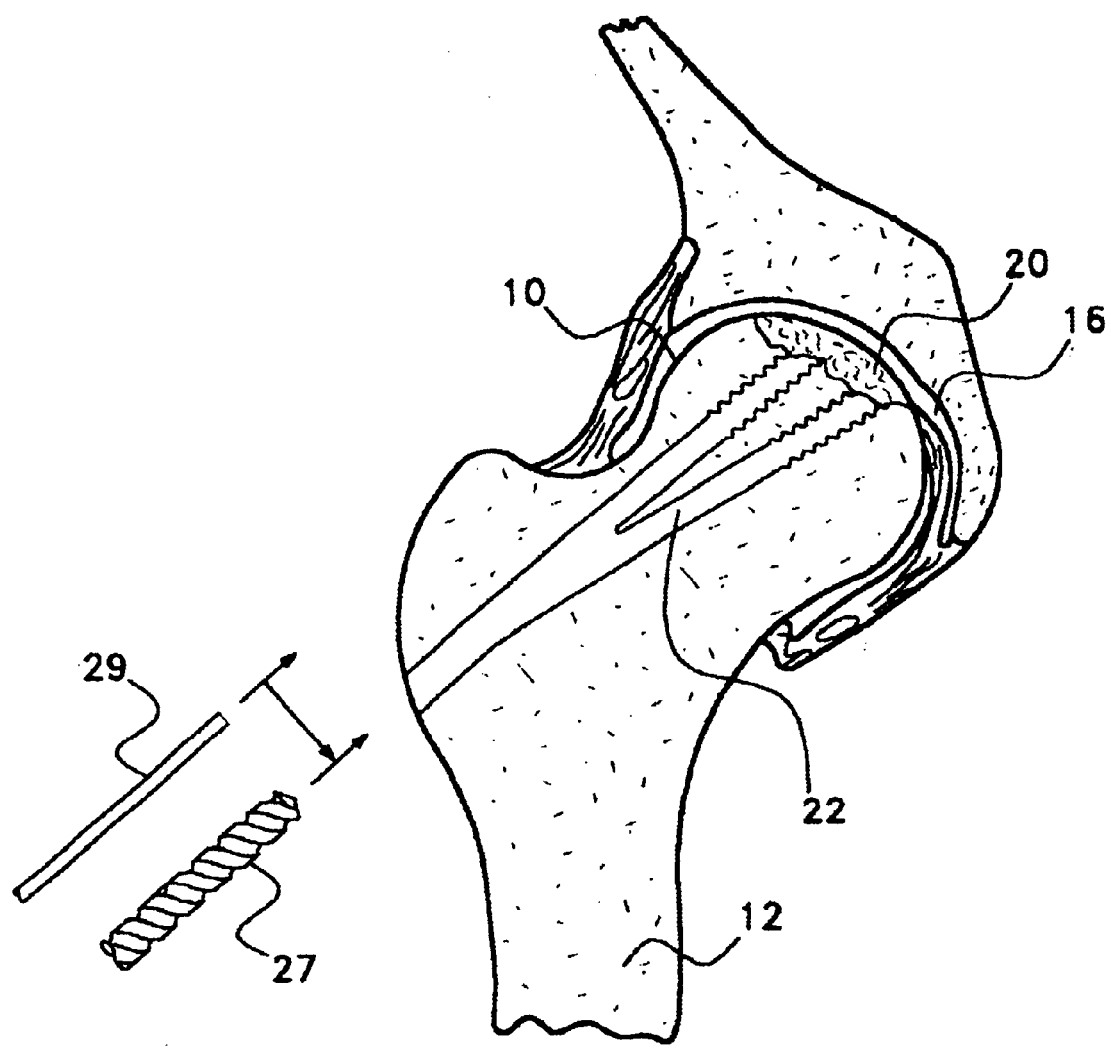
FIG. 3 is the cross-section view of FIG. 1 after having undergone the second step of the present invention treatment method.

Referring to FIG. 3, it will be understood that once each channel 22 is drilled, each channel is extended using a cannular tapping bit 27. The cannular tapping bit 27 extends each channel to the subchondral bone and into the necrotic section 20 of the bone. Each channel 22 is terminated at a distal end that is between two and seven millimeters below the articular cartilage 16.

As the cannular tapping bit 27 extends the channels 22, the section of the channels 22 created by the cannular tapping bit 27 are internally threaded. This threaded section comprises between thirty five percent and ten percent of the overall length of the cannels 22. To assist in the use of the cannular tapping bit 27, guide wires 29 can be placed in each cannel 22 as the cannular tapping bit 27 is advanced. The guide wires 29 help guide the cannular tapping bit 27 and keep the channels 22 straight as the cannular tapping bit 27 extends the length of the channels 22.

Figure 4:
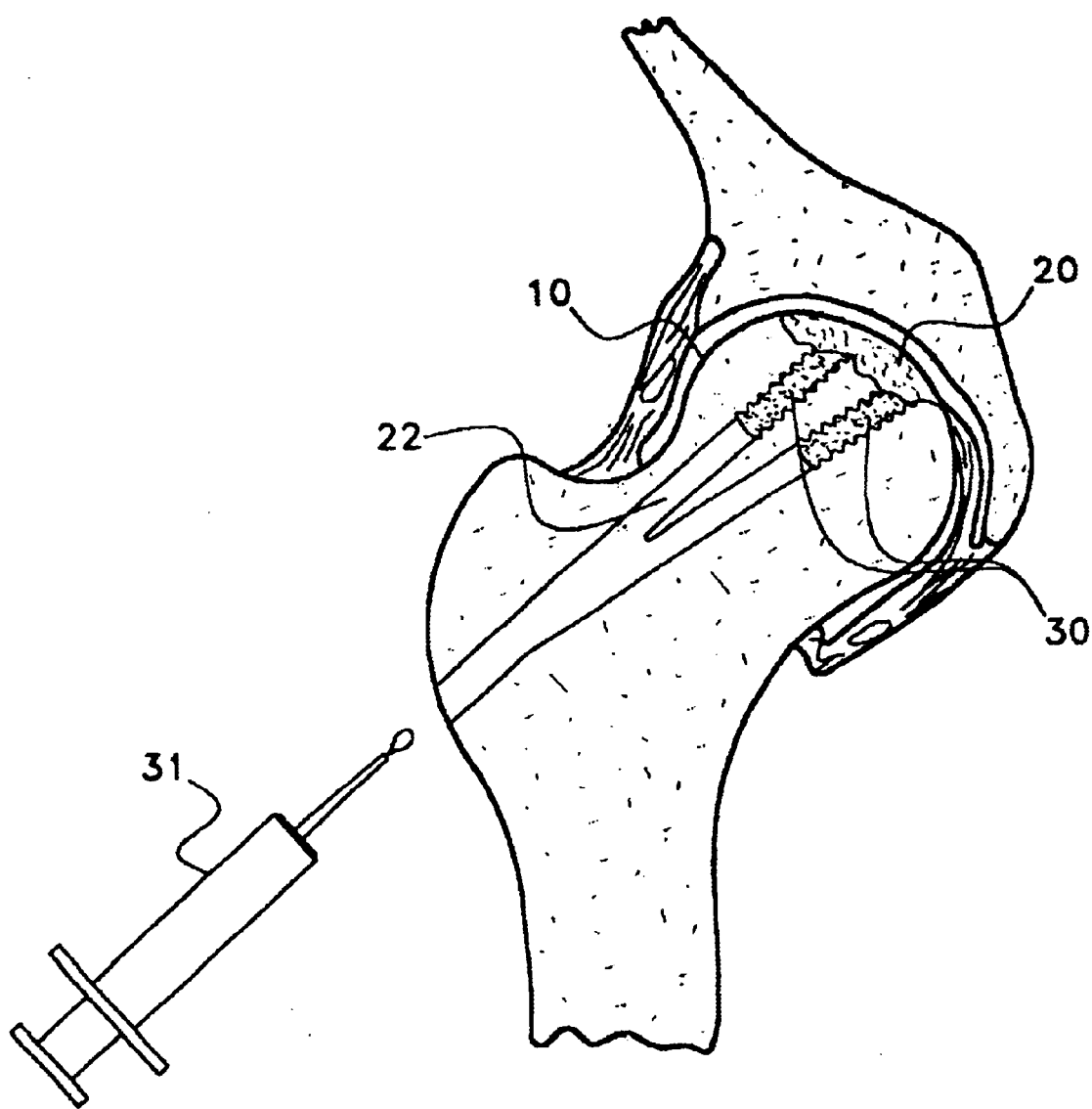
FIG. 4 is the cross-section view of FIG. 1 after having undergone the third step of the present invention treatment method.

Referring to FIG. 4, it can be seen that after the tapping procedure is complete, tools and guides are removed and a volume of a bone growth inducing compound 30 is introduced into each channel 22 using a tuberculin syringe 31 or other similar insertion device. The bone growth inducing compound 30 is any compound that can induce the rapid growth of bone in the human body. Such bone growth inducing compounds typically include bone morphogenetic protein, growth factors and angiogenic factors. Optional bioreactive compositions, such as antibiotics may also be present on the compound. Such bone growth inducing compounds are commercially available under a variety of trademarks, including Osteofil, Regenafil, Regenaform, Opteform, Regenapack, Osteopack, Grafton, Ignite, ICS, Allomatrix and OP-1. However, any other bone growth inducing compound that is known in the art or becomes known in the art can be adapted for use as part of the present invention.

Figure 5:
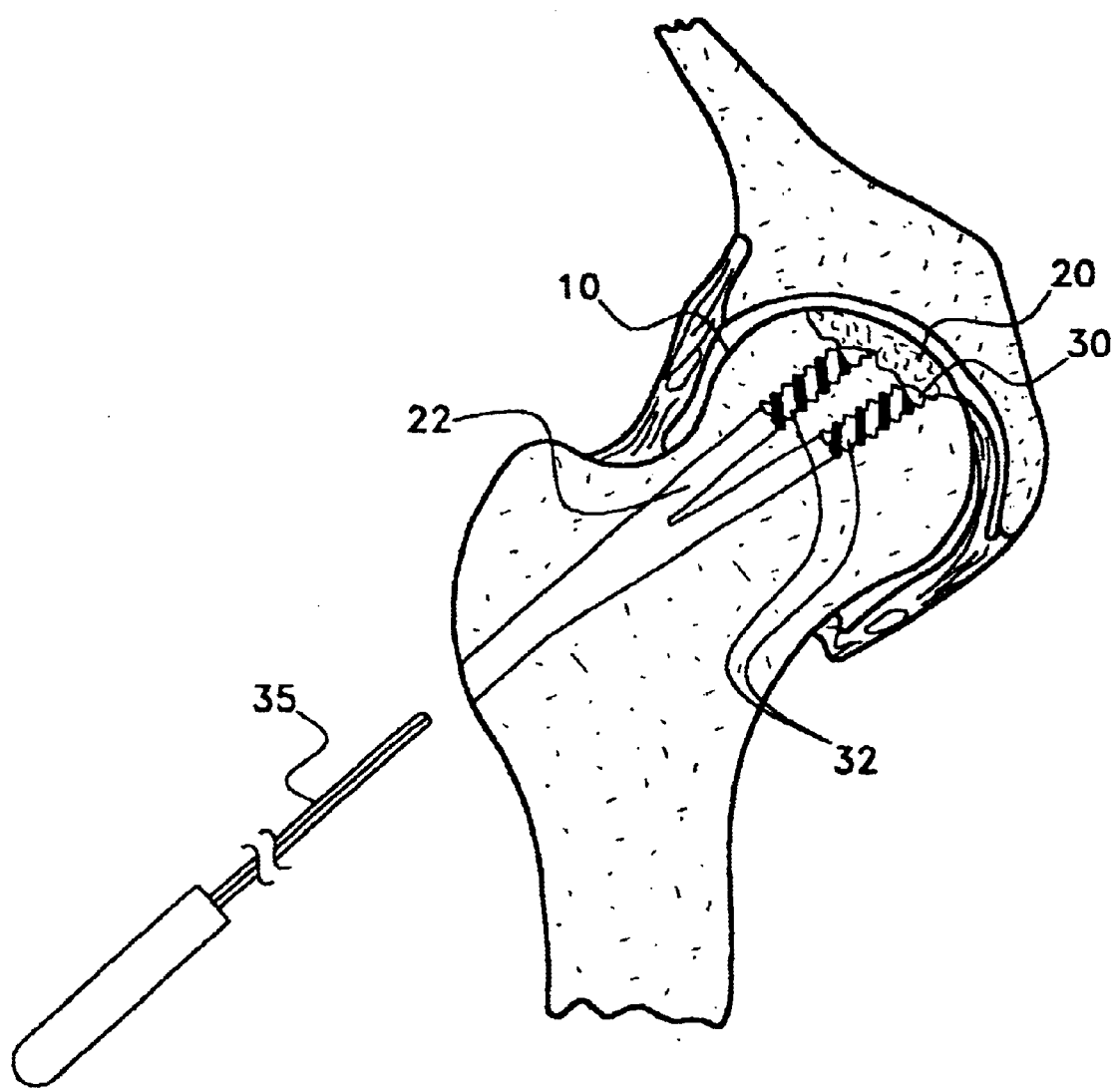
FIG. 5 is the cross-section view of FIG. 1 after having undergone the fourth step of the present invention treatment method.

Referring to FIG. 5, it can be seen that once a volume of the bone growth inducing compound 30 is introduced into each channel 22, proximate the necrotic section 20 of bone, the channels 22 are sealed with a screw 32. The screw 32 is advanced into each channel 22 until the screw engages the internally threaded region at the distal end. The screw 32 is then turned and engages the threading. As the screws 32 are tightened, the screws compact the bone growth inducing compound 30 and bias the bone growth inducing compound toward the distal end of the channel 22. As the bone growth inducing compound 30 is advanced by the screw, the bone growth inducing compound 30 is forced to permeate into the necrotic section 20 of bone. The bone growth inducing compound 30, therefore, permeates and fills any voids in the necrotic section 20 of bone.

The presence of the screws 32 in the distal ends of the channels 22, reinforces the subchondral bone and adds substance to the necrotic section of bone into which the screw passes. Accordingly, the presence of the screws 32 in the channels 22 instantly adds increased structural strength to the necrotic bone that was previously in danger of collapse. If long screws are used, the screws may extend into the neck of the femur. The presence of the screws acts as reinforcement rods, adding significant strength to the femoral neck.

The screws 32 used to seal the channels and compress the bone growth inducing compound 30 are preferably twenty five millimeters to thirty five millimeters in length. Two families of materials can be used in the formation of the screws. Those families of material include biocompatible materials and inert metals. Biocompatible material, such as demineralized bone matrix, human donor bone, and bovine bone can be used to fabricate the screws. The screws can also be fabricated in part or whole by bioresorbable substances, such as polylactic acid polyglycolic acid and like compounds. Such biocompatible materials are demineralized and can be permeated with bone morphogenetic proteins and/or growth factors. Such biocompatible screws are either absorbed or integrated into the femur over time.

Inert metal screws include, screws made from titanium, chrome-cobalt, titanium alloys, tantalum and stainless steel. Such metal screws manufactured to be porous and/or can be coated or textured to promote bonding with growing bone.

As is shown in FIG. 5, the head of the screw 32 contains a shaped recess that enables the screw 32 to be tightened into the channel 22 using an appropriately shaped tightening tool 35.

Figure 6:
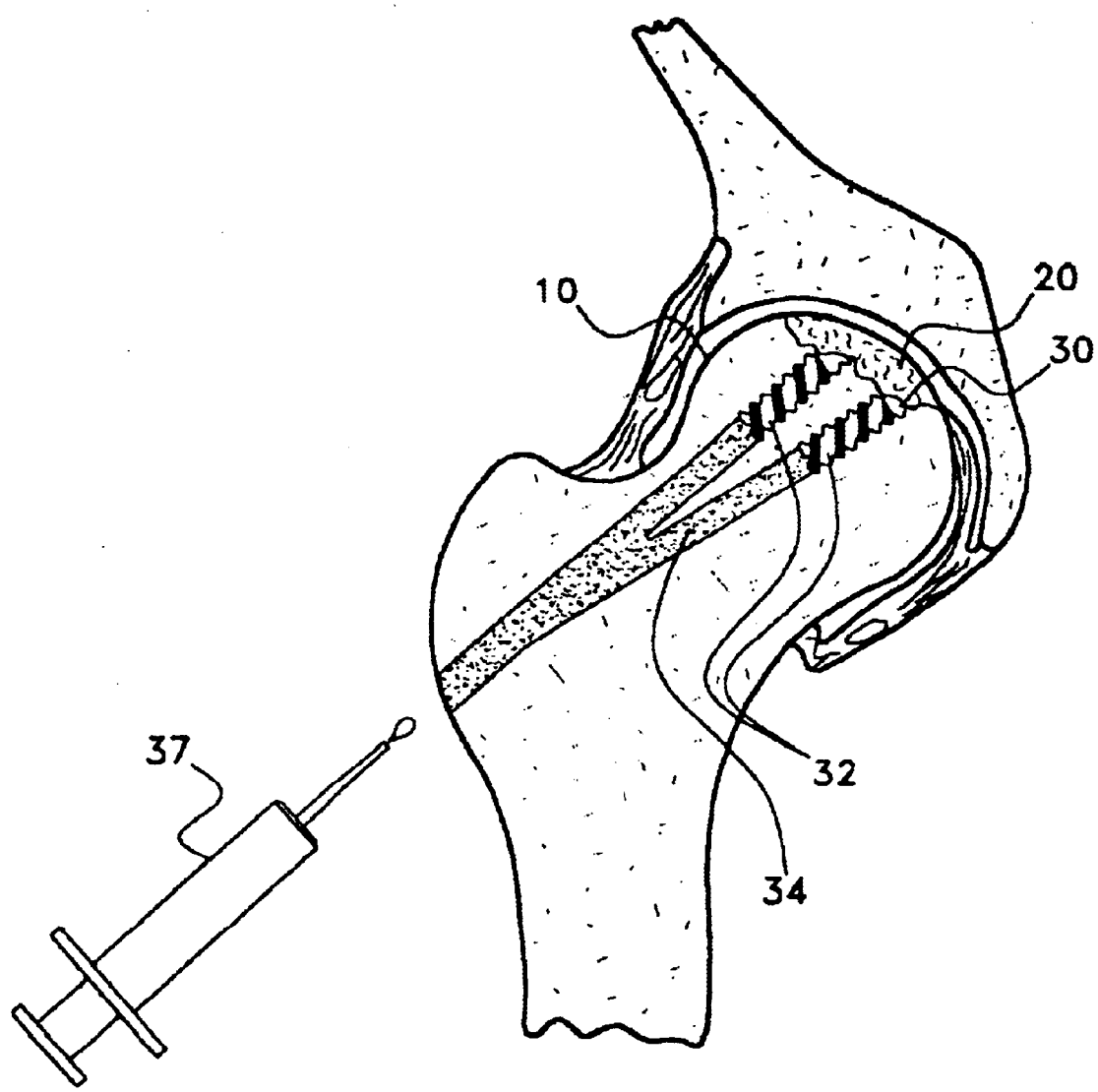
FIG. 6 is the cross-section view of FIG. 1 after having undergone the fifth step of the present invention treatment method.

Referring now to FIG. 6, it can be seen that after the screws 32 are set in place, the remainder of the channels 22 on the side of the screw 32 facing the original drill opening are filled with a bone fill material 34. The bone fill material 34 is preferably a composition made of corticocancellous bone chip and demineralized bone paste. However, any known bone hole fill material used in the prior art can be adapted for use to serve this purpose The bone fill material 34 is again introduced into the channels 22 with a syringe 37.

After undergoing the procedure previously described, the patient is left with a volume of bone growth inducing material 30 permeated throughout the necrotic section 20 of bone. The bone growth inducing material 30 promotes the rapid growth of bone in the necrotic section 20. Furthermore, a screw is now present in the subchondral bone that extends into the necrotic bone. This provides instant structural support to the effected section of bone, thereby preventing collapse of the necrotic section during healing. The result is that the necrotic section 20 is reinforced with the rapid growth of new bone. This heals the necrotic section 20, restoring the patient to health.

It will now be understood that in order for a surgeon to perform the present invention method of treatment that was just described, the surgeon must be provided with a system of tools and materials. These tools and materials include the drill bit 23 shown in FIG. 2; the tapping bit 27 shown in FIG. 3; the guide wire 29 shown in FIG. 3; the syringe 31 of bone growth inducing compound 30 shown in FIG. 4; the screws 32 shown in FIG. 5; the screw tightening tool 35 shown in FIG. 5; and the syringe 37 of fill material 34 shown in FIG. 6. This combination of tools and materials can be prepackaged for a surgeon in the form of a kit.

It will be understood that the embodiment of the present invention system and method that are described and illustrated herein are merely exemplary and a person skilled in the art can make many variations to the embodiment shown without departing from the scope of the present invention. For example, there are many types of cutting bits and reamers that can be used to cut and tap the channels in the bone. Furthermore, there are many other structures, other than screws, that can be used to isolate bone growth inducing compound within the channels. All such variations, modifications and alternate embodiments are intended to be included within the scope of the present invention as defined by the appended claims.

What is claimed is:

1. A method of treating a necrotic section of bone that contains voids, comprising the steps of:

drilling at least one channel in said bone, wherein said at least one channel has a distal end that terminates proximate said necrotic section;

inserting a predetermined volume of bone growth inducing compound into said at least one channel;

inserting a plug into said at least one channel;

advancing said plug into said at least one channel to a point where said plug compresses said bone growth inducing compound in an area of said at least one channel ahead of said plug; and continuing to advance said plug so that said area of said at least one channel ahead of said plug has a volume smaller than said predetermined volume of said bone growth inducing compound, wherein said bone growth inducing compound is displaced out said at least one channel and into said void in said necrotic section of bone.

2. The method according to claim 1, further including the step of tapping a thread within said at least one channel proximate said distal end of said at least one channel.

3. The method according to claim 1, wherein said step of drilling at least one channel in said bone includes drilling into said bone from an entry point and drilling multiple channels toward said necrotic section of bone, wherein each of said channels commonly diverge from said entry point.

4. The method according to claim 1, wherein said necrotic section of bone is in a femoral head and said at feast one channel is drilled through the femoral neck into said femoral head.

5. The method according to claim 1, wherein said bone growth inducing compound includes bone morphogenetic protein, growth factors and angiogenic factors.

6. The method according to claim 1, further including the step of filling said at least one channel with a fill material after said plug has been inserted into said at least one channel.

7. The method according to claim 6, wherein said fill material contains bone chip and demineralized bone paste.

8. The method according to claim 1, wherein said plug is a screw that engages said at least channel with a thread.

9. The method according to claim 8, wherein said screw is made of bone.

10. The method according to claim 8 wherein said screw is made of an inert metal, selected from a group consisting of tantalum, titanium, chrome-cobalt, stainless steel and alloys thereof.

11. A method of treating osteonecrosis in the femur heads comprising the steps of:

drilling at least one channel into the subchondral bone of the femoral head through the neck of the femur, wherein each channel does not pierce the femoral head;

inserting a predetermined volume of bone growth inducing compound into said at at least one channel;

inserting a support into said at least one channel, wherein said support structurally reinforces said femoral head;

advancing said support into said at least one channel to a point where each said support compresses said bone growth inducing compound in an area of said at least one channel ahead of said support;

continuing to advance said support so that said area of said at least one channel ahead of said has a volume smaller than said predetermined volume of said bone growth inducing compound, wherein said bone growth inducing compound is displaced out said at least one channel and into said void in said subchondral bone of said femoral head.

12. The method according to claim 11, wherein said support is a screw that engages said at least one channel with a thread.

13. The method according to claim 11, wherein said step of drilling at least one channel includes drilling into the subchondral bone from an entry point and drilling multiple channels toward the subchondral bone, wherein each of said channels commonly diverge from said entry point.

* * * * *